United States Patent
Chadwick et al.

(10) Patent No.: US 7,175,700 B2
(45) Date of Patent: Feb. 13, 2007

(54) YTTERBIUM-BARIUM SILICATE RADIOPAQUE GLASSES

(75) Inventors: Thomas C. Chadwick, Nipomo, CA (US); Rebecca K. Santiago, Santa Maria, CA (US)

(73) Assignee: Den-Mat Corporation, Santa Maria, CA (US)

( * ) Notice: Subject to any disclaimer, the term of this patent is extended or adjusted under 35 U.S.C. 154(b) by 221 days.

(21) Appl. No.: 10/882,189

(22) Filed: Jul. 2, 2004

(65) Prior Publication Data

US 2006/0014883 A1    Jan. 19, 2006

(51) Int. Cl.
*C08K 3/40* (2006.01)
*A61K 6/08* (2006.01)

(52) U.S. Cl. ............... 106/35; 523/117; 523/116; 523/115; 524/847

(58) Field of Classification Search .............. None
See application file for complete search history.

(56) References Cited

U.S. PATENT DOCUMENTS

| | | | |
|---|---|---|---|
| 3,468,682 A * | 9/1969 | Janakirama-Rao | 501/57 |
| 3,911,581 A | 10/1975 | Dietz | |
| 4,226,627 A * | 10/1980 | Inoue et al. | 501/50 |
| 4,375,967 A | 3/1983 | Schaefer | |
| 4,390,638 A * | 6/1983 | Mennemann et al. | 501/77 |
| 4,629,746 A | 12/1986 | Michl et al. | |
| 4,696,955 A | 9/1987 | Kuhlmann | |
| 4,767,798 A | 8/1988 | Gasser et al. | |
| 5,204,398 A | 4/1993 | Cohen et al. | |
| 5,360,770 A | 11/1994 | Chadwick | |
| 5,883,153 A * | 3/1999 | Roberts et al. | 523/116 |
| 6,297,181 B1 * | 10/2001 | Kunert et al. | 501/57 |
| 6,512,879 B1 * | 1/2003 | Beguin et al. | 385/142 |

* cited by examiner

*Primary Examiner*—C. Melissa Koslow
(74) *Attorney, Agent, or Firm*—Crowell & Moring LLP; John W. Ryan

(57) ABSTRACT

A family of radiopaque glasses comprising silicon dioxide (15–30%), ytterbium oxide (5–35%), barium oxide (30–50%) and fluoride (5–20%), all by weight. The family of glasses all exhibit high radiopacity with refractive indices varying from 1.508–1.592 and translucency ranging from clear to moderately opaque. These glasses can be incorporated into dental composites to provide radiopaque dental restoratives with a desired translucence and appearance.

5 Claims, No Drawings

YTTERBIUM-BARIUM SILICATE RADIOPAQUE GLASSES

BACKGROUND OF THE INVENTION

1. Field of the Invention

This invention relates to radiopaque glasses that are useful as fillers for dental composites.

2. Related Art

Dental restoratives are well known in the art. It is also well known in the art that radiopacity is an important property for a restorative to exhibit. The primary reason for imparting radiopacity to dental restoratives is to facilitate the radiographic diagnosis of dental caries (S. Brent Dove, DDS, MS, "Radiographic Diagnosis of Dental Caries", available on the web at http://www.nidr.nih.gov/news/CONSENSUS/Brent_DoveA.pdf, Retrieved 12 Apr. 2004). Dental caries formation is accompanied by demineralization of enamel or dentin. Caries are diagnosed by examining dental x-rays for evidence of calcium removal. In order to accurately carry out the diagnosis, the surrounding tissue and dental restoratives must be reasonably radiopaque to provide contrast with demineralized, carious areas. Enamel has a reasonable level of radiopacity due to the presence of calcium in the hydroxylapatite that is a component of both enamel and dentin. When restoratives are placed in dentin or enamel they must be at least as radiopaque as the surrounding healthy hard tissue or the restored areas could be mistakenly identified as carious tissue. Certain well known restoratives such as amalgam zinc phosphate cement, zinc oxide eugenol cement, gold foil or castings as well as other metallic restoratives present no problems regarding radiopacity.

Composite restoratives offer an alternative to these older restoratives. Composites contain two primary components, a resin phase and a filler phase. Composites can be handled easily by the dentist, are usually well tolerated without any irritation by the patient, ensure an aesthetically attractive appearance of the filling, and offer the possibility to move away from amalgam filling materials which have been criticized for physiological reasons. However, the radiolucence of composites can be a big problem, since the resin portion of the composite is not normally radiopaque and the fillers that reinforce the resin may not be either.

Several efforts have been made to impart radiopacity to composite restoratives. They all generally involve trying to incorporate elements with high atomic numbers in either the filler or the resin phase. Chadwick teaches a family of oxyfluoride glasses that contain strontium and/or barium to impart radiopacity, U.S. Pat. No. 5,360,770. Kuhlmann teaches using radiopaque monomers to form a radiopaque resin, U.S. Pat. No. 4,696,955. Dietz teaches the use of barium oxide aluminosilicate glass, U.S. Pat. No. 3,911,581. Michl, et al. describe various prior art compositions including the use of barium sulfate to provide a radiopaque filler, U.S. Pat. No. 4,629,746, col. 1, lines 12–62. Schaefer describes a radiopaque filler for dental composites that incorporates zeolites containing one or more of the elements calcium, strontium, barium, lanthanum, rare earth elements with atomic numbers 58–71, tantalum and hafnium, U.S. Pat. No. 4,375,967. Gasser, et al. describe the use of calcium, strontium and barium salts of hexafluorotitanate, -zironate and -hafnate ($TiF_6$, $ZrF_6$ and $HfF_6$) as well as yttrium fluoride to impart radiopacity to the filler, U.S. Pat. No. 4,767,798. Various compounds containing rare earths have also been proposed as composite fillers for imparting radiopacity. Michl, et al. teach the use of rare earth metal fluorides in amounts of 1% to 50% (elements with atomic numbers from 57–71) as radiopaquing fillers in dental composites, U.S. Pat. No. 4,629,746. They indicate that the rare earth fluorides are particularly well suited for this task because they are more translucent than other rare earth compounds. Cohen, et al. teach dental cement compositions containing lanthanide compounds (oxide, carbonate, nitrate or chloride are used in the examples) in the amount of 1–20%. They state that the lanthanide compounds " . . . substantially increase the strength of the composition" and they also added fluorides (ytterbium fluoride among them) in amounts up to 6.0%. Although increasing composite strength was the primary stated reason for adding these compounds, another likely unstated reason was to impart radiopacity, U.S. Pat. No. 5,204,398.

Many of these prior approaches involved using a single substance or a small group of substances, to impart radiopacity. Very little choice was available as far as visual translucency was concerned and the use of elements with atomic numbers less than that of ytterbium (70) was not optimal for imparting radiopacity. Moreover, some of the radiopacifiers, such as the brominated monomers of U.S. Pat. No. 4,696,955 may not be safe.

Accordingly, it would be desirable to provide a composite dental restorative composition having a high degree of radiopacity whose translucency could be varied depending on the desired dental application.

SUMMARY OF THE INVENTION

One embodiment of the invention is to provide a family of glasses with varying degrees of visual translucency and a high degree of radiopacity. Their incorporation into dental composites as fillers will impart radiopacity to the resulting composites. Since members of this glass family exhibit varying degrees of visual translucency, judicious choice of filler glass can be used to adjust the appearance of the resulting composite while maintaining a high level of radiopacity.

Another embodiment of the invention is to provide a family of glasses with ytterbium oxide ($Yb_2O_3$) as an important component with varying degrees of visual translucency and a high degree of radiopacity. Their incorporation into dental composites as fillers will impart radiopacity to the resulting composites. Since members of this glass family exhibit varying degrees of visual translucency, judicious choice of filler glass can be used to adjust the appearance of the resulting composite while maintaining a high level of radiopacity.

Another embodiment of the invention is to provide a family of glasses varying from 4 components to 7 components with varying degrees of visual translucency and a high degree of radiopacity. Their incorporation into dental composites as fillers will impart radiopacity to the resulting composites. Since members of this glass family exhibit varying degrees of visual translucency, judicious choice of filler glass can be used to adjust the appearance of the resulting composite while maintaining a high level of radiopacity.

A further embodiment of the invention is to provide a family of glasses with varying degrees of visual translucency and a high degree of radiopacity with barium oxide (BaO) or strontium oxide (SrO) used in addition to $Yb_2O_3$ to impart radiopacity. Their incorporation into dental composites as fillers will impart radiopacity to the resulting composites. Since members of this glass family exhibit varying degrees of visual translucency, judicious choice of filler glass can be used to adjust the appearance of the resulting composite while maintaining a high level of radiopacity.

A further embodiment of the present invention is to provide a method for controlling the translucence of dental composites by judicious choice of radiopaque glass compositions ranging from 4 to 7 components.

DESCRIPTION OF THE INVENTION

The glass compositions of the present invention are comprised of 4, 5, 6 or 7 components. All glass compositions of the present invention comprise at least the following compounds in varying molar ratios: silicon dioxide ($SiO_2$), $Yb_2O_3$, fluoride (F) and MO, wherein M is either Ba or Sr. The five component glass compositions additionally comprise aluminum oxide ($Al_2O_3$) or phosphorus pentoxide ($P_2O_5$). The six component glass compositions additionally comprise $Al_2O_3$ and $A_2O$ wherein A is either sodium (Na) or potassium (K); or additionally comprise $Al_2O_3$ and $P_2O_5$; or additionally comprise boric anhydride ($B_2O_3$) and $Na_2O$. The seven component glass compositions additionally comprise $Al_2O_3$, $P_2O_5$ and $A_2O$ wherein A is either K or Na.

The glasses of the present invention were developed to provide high levels of radiopacity to composites while at the same time providing a range of visual appearance. These glasses were formulated to contain up to 45.4% of BaO and up to 33.7% of $Yb_2O_3$, two very radiopaque compounds (all by weight). Strontium could also be substituted for barium. By maintaining very high levels of radiopaque elements in these glasses, the present invention provides substantial levels of radiopacity to composites at a relatively low percentage of fill, thus allowing the use of other fillers with favorable properties such as high strength to be used concurrently. The present invention also presents glasses with a range of visual appearances ranging from clear to opalescent to opaque thus providing a range of glass fillers that could impart a variety of optical effects to the composites into which they were incorporated. Sometimes it is desirable to impart opacity to a composite, sometimes opalescence and sometimes clarity, but all these glasses can deliver substantial radiopacity to the composites made from them. Thus, the present invention provides diagnostic utility as well as aesthetic choice to dental composites.

Based on the requirement for radiopacity, the four best glasses are $SiO_2$—$Al_2O_3$—$P_2O_5$—$K_2O$—BaO—$Yb_2O_3$—F (Example 15)>$SiO_2$—BaO—$Yb_2O_3$—F (Example 1)>$SiO_2$—$Al_2O_3$—$P_2O_5$—$Na_2O$—BaO—$Yb_2O_3$—F (Example 11)>$SiO_2$—$Al_2O_3$—$K_2O$—BaO—$Yb_2O_3$—F (Example 7). These same four glasses are also the most translucent, but the order for translucency is $SiO_2$—$Al_2O_3$—$K_2O$—BaO—$Yb_2O_3$—F>$SiO_2$—$Al_2O_3$—$P_2O_5$—$Na_2O$—BaO—$Yb_2O_3$—F>$SiO_2$—$Al_2O_3$—$P_2O_5$—$K_2O$—BaO—$Yb_2O_3$—F>$SiO_2$—BaO—$Yb_2O_3$—F. $SiO_2$—BaO—$Yb_2O_3$—F exhibited slightly greater water solubility than the other three. These four glasses represent the most preferred embodiment of the invention. See Table 2 for the compositions of each glass.

The glasses of this invention can be prepared by conventional methods. The desired components can be placed in a vessel and thoroughly mixed. The vessel can then be subjected to a heating cycle to form a glass melt. This is commonly known in the art as crucible melting. The glass melt can then be cooled such as by pouring it into cool water. Cooled glass fragments can then be washed and dried.

The prepared glasses of this invention can then be used to prepare composite dental restoratives by conventional methods. The glasses can be mixed with a resin and other fillers in a mixing vessel. The resins can be chosen such that the refractive index of the resin and glass filler substantially match. After formulation the composite can then be molded and subjected to a curing cycle to form the cured composite.

EXAMPLES

Synthesis of Glasses Raw Materials

Silicon dioxide (Sil-Co-Sil 90, US Silica Company, 99.8%), aluminum fluoride (Alcan Smelter and Chemicals, Ltd., 91% on fluorine), barium fluoride (Barium and Chemicals, 99.4%), barium carbonate (Laguna Clay Co., 99%), hydrated alumina (Alcoa Industrial Chemicals, 99.5% on $Al_2O_3$), cryolite, sodium fluoride (J. T. Baker, U.S.P.), potassium fluoride (ACS Reagent), ammonium dihydrogen phosphate (Astaris, 99%), ytterbium fluoride (Pacific Industrial Development Corporation, 99.9% metals purity) and ytterbium oxide (Pacific Industrial Development Corporation, 99.9%) were used as received from the manufacturers. Aluminum orthophosphate was synthesized by intimately mixing hydrated aluminum oxide, 92.1 g (1.18 mol) and ammonium dihydrogen phosphate, 135.9 g (1.18 mol). The mixture was placed in a clay bonded, fused silica crucible, brought to 820° C. in 2.3 hours and held at 820° C. for 3.0 hours. Barium orthophosphate was synthesized by intimately mixing barium carbonate, 592.0 g (3.00 mol) and ammonium dihydrogen phosphate, 230.1 g (2.00 mol). The mixture was placed in two clay bonded, fused silica crucibles and fired at 316° C. for 13.5 hours, 600° C. for 6.0 hours and 1000° C. for 4.3 hours. All materials were ground as necessary and screened through a 100 mesh US Series Screen prior to use. This invention is not limited to glasses incorporating aluminum orthophosphate, barium orthophosphate or their precursors, nor is it limited to aluminum orthophosphate or barium orthophosphate prepared in this manner. The starting materials could also be used directly. Also, the choice of starting materials is not important and others could be used to form the glasses of this invention.

Synthesis of Glasses: Glass Batching and Firing

Raw materials for the batch were first screened, if necessary, to ensure that all raw materials passed a 100 mesh US Series screen. The raw materials were then weighed, placed in a baffled mixing jar, and the jar was rolled for 2 hours at 1 Hz to ensure thorough blending of the ingredients. After blending, the raw materials were packed into a clay bonded, fused silica crucible (4.25 in. (10.8 cm) top diameter, 6.00 in. (15.2 cm) tall, Size "I" crucible, DFC Thermal Ceramics, Canon City, Colo.). Tapping the crucible on a hard surface between powder additions eliminated air in the powder. The crucible with its contained mixture was fired in a Thermolyne High Temperature Muffle Furnace (Model F46230CM) equipped with a programmable controller. The same firing program was used for firing all the glasses made for this study.

The furnace was programmed for the following firing sequence: Step 1—Heating Rate 14° C./min, Max Temp 400° C., no dwell: Step 2—Heating Rate 6° C./min, Max Temp 730° C., no dwell; Step 3—Heating Rate 3° C./min, Max Temp 1000° C., no dwell; Step 4—Heating Rate 1° C./min, Max Temp 1180° C., no dwell; Step 5—Heating Rate 0° C./min, Max Temp 1180° C., 180 minute dwell; Step 6—End. At the end of the firing cycle, the crucible was withdrawn from the furnace and the glass melt was poured into cool (20° C.) water. The glass fragments were collected on a Buchner funnel, washed three times with distilled water and dried to constant weight at 105° C. The batch, crucible and lid weights were recorded before firing, and the recovered glass, crucible and lid weights were recorded after firing in order to construct a material balance for each firing.

Example 1

A four component glasses $SiO_2$—$BaO$—$Yb_2O_3$—$F$ was formed using the starting materials listed in Table 1. Table 1 further compares the four component glasses to known class (770).

Example 2

A five component glass $SiO_2$—$Al_2O_3$—$BaO$—$Yb_2O_3$—$F$ was formed using the starting materials listed in Table 1.

Examples 3–4

Two five component glasses $SiO_2$—$P_2O_5$—$BaO$—$Yb_2O_3$—$F$ were formed using the starting materials listed in Table 1.

Examples 5–6

Two six component glasses $SiO_2$—$Al_2O_3$—$Na_2O$—$BaO$—$Yb_2O_3$—$F$ were formed using the starting materials listed in Table 1.

Example 7

A six component glass $SiO_2$—$Al_2O_3$—$K_2O$—$BaO$—$Yb_2O_3$—$F$ was formed using the starting materials listed in Table 1.

Example 8–9

Two six component glasses $SiO_2$—$Al_2O_3$—$P_2O_5$—$BaO$—$Yb_2O_3$—$F$ were formed using the starting materials listed in Table 1.

Example 10

One six component glass $SiO_2$—$B_2O_3$—$Na_2O$—$BaO$—$Yb_2O_3$—$F$ was formed using the starting materials listed in Table 1.

Examples 11–14

Four seven component glasses $SiO_2$—$Al_2O_3$—$P_2O_5$—$Na_2O$—$BaO$—$Yb_2O_3$—$F$ were formed using the starting materials listed in Table 1.

Example 15

A seven component glass $SiO_2$—$Al_2O_3$—$P_2O_5$—$K_2O$—$BaO$—$Yb_2O_3$—$F$ was formed using the starting materials listed in Table 1.

Examples 16–17

Two seven component glasses $SiO_2$—$Al_2O_3$—$P_2O_5$—$Na_2O$—$SrO$—$Yb_2O_3$—$F$ were formed using the starting materials listed in Table 1.

The weight percents of each compound in the formed glasses for each example are shown in Table 2. Table 2 further compares each of the compound glasses with known glass (770).

TABLE 1

Starting Materials for Each Glass (Parts by weight)

| Ex. | $SiO_2$ | $Al(OH)_3$ | $AlF_3$ | $AlPO_4$ | $NaAlF_6$ | $NaF$ | $KF$ | $Yb_2O_3$ | $YbF_3$ | $BaF_2$ | $Ba_3(PO_4)_2$ | $SrF_2$ | $H_3BO_3$ |
|---|---|---|---|---|---|---|---|---|---|---|---|---|---|
| 1 | 98.2 | — | — | — | — | — | — | 70 | — | 181.8 | — | — | — |
| 2 | 70.2 | 26.2 | 15.1 | — | — | — | — | 66.3 | — | 172.3 | — | — | — |
| 3 | 92.4 | — | — | — | — | — | — | 69.7 | — | 134.5 | 53.4 | — | — |
| 4 | 92.4 | — | — | — | — | — | — | — | 81.34 | 134.5 | 53.4 | — | — |
| 5 | 73.5 | 27.5 | 11.5 | — | 10.8 | — | — | 69.4 | — | 166.9 | — | — | — |
| 6 | 67.07 | 50.92 | 11.09 | — | 10.4 | — | — | 67.01 | — | 161.1 | — | — | — |
| 7 | 73.5 | 27.5 | 15.82 | — | — | — | 8.97 | — | — | 166.9 | — | — | — |
| 8 | 66.3 | 24.8 | 14.2 | 19.4 | — | — | — | 62.6 | — | 162.7 | — | — | — |
| 9 | 66.3 | 24.8 | 14.2 | 19.4 | — | — | — | — | 73.08 | 162.7 | — | — | — |
| 10 | 73.5 | — | — | — | — | 6.5 | — | 69.5 | — | 167.1 | — | — | 33.4 |
| 11 | 53.3 | — | 9.75 | 18.29 | 9.14 | — | — | 117.8 | — | 141.7 | — | — | — |
| 12 | 39.3 | 30.92 | 7.19 | 13.48 | 6.74 | — | — | 8.68 | — | 104.4 | — | — | — |
| 13 | 38.08 | 26.64 | 6.97 | 13.07 | 6.53 | — | — | 16.82 | — | 101.2 | — | — | — |
| 14 | 186.3 | 81.44 | 34.07 | 63.87 | 31.94 | — | — | 205.73 | — | 494.9 | — | — | — |
| 15 | 53.3 | — | 13.41 | 18.29 | — | — | 7.59 | 117.8 | — | 141.7 | — | — | — |
| 16 | 40.08 | 17.52 | 7.33 | 13.74 | 6.87 | — | — | 44.26 | — | — | — | 76.27 | — |
| 17 | 44.45 | 31.09 | 8.13 | 15.24 | 7.62 | — | — | 19.64 | — | — | — | 84.6 | — |
| (770) | 175 | 153 | 32 | 60 | 30 | — | — | — | — | 464.8 | — | — | — |

TABLE 2

Weight Percent Elemental Composition of Glasses

| Example | $SiO_2$ | $Al_2O_3$ | $P_2O_5$ | $B_2O_3$ | $K_2O$ | $Na_2O$ | $BaO$ | $SrO$ | $Yb_2O_3$ | $F$ | <O equiv to F> |
|---|---|---|---|---|---|---|---|---|---|---|---|
| 1 | 28.06 | — | — | — | — | — | 45.43 | — | 20.00 | 11.26 | −4.74 |
| 2 | 20.59 | 7.71 | — | — | — | — | 44.19 | — | 19.44 | 13.95 | −5.88 |
| 3 | 26.40 | — | 3.60 | — | — | — | 45.27 | — | 19.91 | 8.33 | −3.51 |
| 4 | 25.55 | — | 3.48 | — | — | — | 43.81 | — | 19.27 | 13.63 | −5.74 |
| 5 | 21.00 | 7.88 | — | — | — | 1.37 | 41.69 | — | 19.82 | 14.24 | −5.99 |

TABLE 2-continued

Weight Percent Elemental Composition of Glasses

| Example | SiO$_2$ | Al$_2$O$_3$ | P$_2$O$_5$ | B$_2$O$_3$ | K$_2$O | Na$_2$O | BaO | SrO | Yb$_2$O$_3$ | F | <O equiv to F> |
|---|---|---|---|---|---|---|---|---|---|---|---|
| 6 | 19.17 | 12.16 | — | — | — | 1.32 | 40.26 | — | 19.15 | 13.74 | −5.79 |
| 7 | 21.00 | 7.88 | — | — | 1.37 | — | 41.69 | — | 19.82 | 14.24 | −5.99 |
| 8 | 19.42 | 9.65 | 3.31 | — | — | — | 41.68 | — | 18.34 | 13.15 | −5.54 |
| 9 | 18.84 | 9.36 | 3.21 | — | — | — | 40.44 | — | 17.79 | 17.90 | −7.54 |
| 10 | 22.33 | — | — | 3.81 | — | 1.46 | 44.40 | — | 21.12 | 11.90 | −5.01 |
| 11 | 15.23 | 4.51 | 3.04 | — | — | 1.16 | 35.41 | — | 33.66 | 12.08 | −5.09 |
| 12 | 19.65 | 15.92 | 3.92 | — | — | 1.49 | 45.65 | — | 4.34 | 15.58 | −6.56 |
| 13 | 19.04 | 14.34 | 3.80 | — | — | 1.45 | 44.22 | — | 8.41 | 15.10 | −6.36 |
| 14 | 17.41 | 10.13 | 3.47 | — | — | 1.32 | 40.45 | — | 19.23 | 13.80 | −5.81 |
| 15 | 15.23 | 4.51 | 3.04 | — | 1.16 | — | 35.41 | — | 33.66 | 12.08 | −5.09 |
| 16 | 20.04 | 11.66 | 4.00 | — | — | 1.52 | — | 31.46 | 22.13 | 15.89 | −6.69 |
| 17 | 22.23 | 16.74 | 4.43 | — | — | 1.69 | — | 34.89 | 9.82 | 17.62 | −7.42 |
| (770) | 20.31 | 17.61 | 4.05 | — | — | 1.54 | 47.17 | — | — | 16.10 | −6.78 |

These glasses only represent exemplary embodiments of this invention and are meant in no way to limit the scope of the appended claims. Those of ordinary skill in the art would recognize that numerous other compounds could be prepared by the same inventive concept. For instance, strontium could be substituted for barium in any of the compounds. Other alkaline earth metals could be substituted for barium or strontium. Other alkali metals could be substituted for sodium or potassium. Additionally, the molar ratios of each component in each composite could also be varied well within the scope of this invention. These are only a few of possible embodiments of this invention that would be readily recognized by those skilled in the art.

Formation of Test Composites

Each glass was incorporated into a simple composite formulation and then fabricated into a test chip that was 15.2 mm in diameter and 0.86 mm thick. The composites were formulated to contain a resin phase that was 83.05% ethoxylated bisphenol-A dimethacrylate, 15.82% urethane dimethacrylate and 1.13% of the curative TPO (all by weight). Each composite also contained an auxiliary quartz filler (99.5% pure SiO$_2$) to help prevent the sedimentation of the filler while chips were being prepared, as well as the glass that was being tested. Preliminary tests established that the total filler content should be held at 55% and the radiopaque glass should be held at 40% of the total filler composition (all by volume). The test composite composition for each glass was 45% resin, 33% quartz filler and 22% radiopaque glass (all by volume).

For purposes of calculating the weight composition of each test composite, the density of the resin was taken as 1.20 g/cm$^3$, the density of the quartz filler was 2.65 g/cm$^3$ and the density of each radiopaque glass was taken from density measurements that had been made previously. The composition (% by weight, $W_k$%) of each component in the test composite was calculated by first multiplying the volume percentage of each component ($V_k$%) by its density ($P_k$), summing all the products, and then multiplying the product for each individual component by 100 and dividing by the sum of products for all components:

$$W_k\% = 100 * V_k\% * \rho_k / \Sigma V_k\% * \rho_k$$

Each composite was formulated by placing the correct amount of resin component in a beaker and adding the fillers, which had been previously weighed and mixed in a separate beaker, in small portions with thorough hand mixing. Chips were made by placing the steel disk mold on a piece of clear Reynolds 914 Film, which was supported on a glass plate, filling the mold with composite, placing another piece of film and a glass plate on the filled mold and curing on both sides of the sample in two 9 second sessions with a Virtuoso Xenon Power Arc Light (Den Mat Corporation, Santa Maria, Calif. 93455).

This method was only used to form composites for testing properties of the glasses such as radiopacity and translucence. Those skilled in the art would first choose a glass of this invention based on the desired translucence of the composite. The resin would then be chosen based on the refractive index of the chosen glass so that the refractive indices would substantially match. The chosen resin and glass could then be incorporated into a composite by conventional methods.

After the glasses were formed, the properties of each was determined. The following properties of the glasses were measured: refractive index, density, and solubility. Composites formed from the glasses were used to measure the radiopacity and translucency. A detailed description of the method of measuring each property is provided below.

Refractive Index (R.I.) Measurements

A sample of each glass was ground to produce 10–20 μm particles and these were examined under crossed polars with a petrographic microscope (Unitron Bio Pol II) to detect the presence of crystalline phases. The approximate volume percent of crystals was estimated where evidence of devitrification was observed. The refractive index of any glass phase present was determined by the Becke Line test (see Clyde W. Mason, "Handbook of Chemical Microscopy, Vol. 1", fourth edition, John Wiley and Sons, New York, 1983, p. 319) using Cargille immersion liquids (n=1.460 to 1.640 in 0.004 increments).

Density

Glass density was determined on ~0.3–0.5 g samples using Archimedes Principle. A 1.00 mL Class A volumetric flask was used as a pycnometer and distilled water was used as the immersion fluid.

Glass Solubility (Hydrolytic Resistance of Glass Grains at 98° C.)

Hydrolytic resistance of glass grains at 98° C. was measured using "Glass—Hydrolytic resistance of glass grains at 98° C.—Method of test and classification" ISO 719 1985 (E).

X-Ray Opacity Measurement

Test chips were formed by the method provided above. Radiopacity measurements were conducted using a procedure that closely followed the work reported by Gurdal and Akdeniz (P. Gurdal and B. G. Akdeniz, "Comparison for Two Methods for Radiometric Evaluation of Resin based Restorative Materials", Dentomaxillofacial Radiology, 27, 236–239 (1998), available on the Internet at http://dmfr.birjoumais.org/cgi/reprint/27/4/236.pdf). Measurements done on the same test specimens using different x-ray images were generally in excellent agreement.

Translucency Evaluation

Test chips were formed in the same manner as provided above except that the quartz filler was not used. Each composite was formulated to contain 22% of the glass that was being tested and 78% of resin (all by volume). The quartz filler was eliminated from these specimens so special care was taken to keep the filler glass in suspension while preparing the test specimens.

Translucency was evaluated in a manner quite similar to that employed by Meng, Chao and Liao. (see Hua Xi Kou Qiang Yi Xue Za Zhi. 2002 October; 20(5):367 9 accessed through Medline PMID: 12607370). Spectra for each chip were scanned on a Shimadzu UV-Vis Spectrometer, Model 1601, between 300 nm and 800 nm. The chips were mounted on a cuvette holder in the sample light beam using adhesive tape to hold them in place and they were measured against an air path reference. The spectra were recorded, printed, scanned and then digitized using ImageTool v. 3.0, by recording absorbance values at 50 nm intervals across each spectrum. The absorbance values as a function of wavelength were saved as *.txt files and imported into EXCEL. All spectra were plotted on the same graph so that direct comparisons of absorbance of the different glasses could be made.

Table 3 shows the properties of each glass tested for these glasses corresponds well to the refractive indices of common dental resins. For example, commonly employed monomers in resins for dental composites include polymerized 1,6-hexandiol dimethacrylate, urethane dimethacrylate and triethyleneglycol dimethacrylate, all with a refractive index of around 1.508; and polymerized ethoxylated bisphenol-A dimethacrylate, with a refractive index of around 1.564. Resins commonly used in dental composites are prepared from blends of these parent monomers and the polymerized blends can be prepared with refractive indices ranging from 1.508 to 1.564.

Glass Translucency

Glasses ranged from very clear to moderately opaque with the four and five component glasses being the most opaque.

Radiopacity

Radiopacity for all these glasses was excellent. For most test composites a radiopacity equivalent to 2.0 mm of aluminum could be achieved in a 0.86 mm composite test chip with only 22% (by volume) of radiopaque glass. This compared favorably to a test composite formed from the glass of U.S. Pat. No. 5,360,770, which exhibited a radiopacity of 1.44.

Glass Solubility

Water solubility for all these glasses was low. In most cases the glasses belonged to the lowest solubility class, HGB-1 (ISO 719-1985 (E)). Three glasses, one four component (Example 1), one five component (Example 3) and one six component glass (Examples 10) belonged to Solubility Class HGB3. None of the glasses exhibited higher solubility.

Although particular embodiments of this invention have been disclosed herein for purposes of explanation, further

TABLE 3

Physical Property Summary

| Example | R.I. | Density g/cm3 | Solubility Class | Radiopacity | Translucence |
|---|---|---|---|---|---|
| 1 | 1.576 | 4.04 | HGB-3 | 3.03 | Opq., ~30% devit. |
| 2 | 1.548 | 4.19 | HGB-1 | 2.48 | Clear, no devit. |
| 3 | 1.592 | 3.97 | HGB-3 | 2.22 | Opq., part. devit. |
| 4 | 1.568 | 3.89 | HGB-1 | 2.22 | Opq., 60% devit. |
| 5 | 1.536–1.540 | 3.94 | HGB-1 | 2.54 | Clear glass, no devit. |
| 6 | 1.540 | 3.95 | HGB-1 | 2.44 | Opq., 25%–50% devit. |
| 7 | 1.536 | 4.03 | HGB-1 | 2.67 | Clear, slightly opalescent. |
| 8 | 1.548 | 3.73 | HGB-1 | 2.16 | Clear, trace devit. |
| 9 | 1.524 | 3.81 | HGB-1 | 1.88 | Clear, no devit. |
| 10 | 1.565 | 4.00 | HGB-3 | 2.41 | Opq., part. devitrified. |
| 11 | 1.572 | 4.40 | HGB-1 | 2.99 | Clear, no devit. |
| 12 | 1.520 | 3.34 | HGB-1 | 1.54 | Clear, no devit. |
| 13 | 1.524–1.528 | 3.55 | HGB-1 | 1.78 | Clear, no devit. |
| 14 | 1.540 | 3.89 | HGB-1 | 2.45 | Clear, minor devit. |
| 15 | 1.564–1.568 | 4.62 | HGB-1 | 3.15 | Opal. |
| 16 | 1.522 | 3.42 | HGB-1 | 2.25 | Clear, no devit. |
| 17 | 1.508 | 3.04 | HGB-1 | 1.36 | Clear, no devit. |
| (770) | 1.520 | 3.60 | HGB-1 | 1.44 | Clear, very minor devit. |

RESULTS

Refractive Index

For the barium-ytterbium glasses, refractive indexes range from 1.520 to 1.592 with an average of 1.549. The two examples of strontium-ytterbium glass had refractive indices of 1.508 and 1.522. In general, increasing the $Yb_2O_3$ content increased the refractive index for both barium ytterbium and strontium-ytterbium glasses. The range of refractive indices modifications or variations thereof will be apparent to those skilled in the art to which this invention pertains. Thus, the scope of the present invention is only limited by the appended claims.

What is claimed is:

1. A composite comprising:
   (a) a resin; and
   (b) a glass filler, said glass filler comprising the following ingredients:

(i) $SiO_2$;
(ii) $Yb_2O_3$;
(iii) F;
(iv) BaO; and
(v) at least one component selected from the group consisting of $Al_2O_3$, $P_2O_5$, $Al_2O_3$—$Na_2O$, $Al_2O_3$—$K_2O$, $Al_2O_3$—$P_2O_5$, $Al_2O_3$—$P_2O_5$—$Na_2O$ and $Al_2O_3$—$P_2O_5$—$K_2$.

2. The composite according to claim 1 wherein said composite is substantially radiopaque.

3. The composite according to claim 2, wherein said composite is substantially clear.

4. The composite according to claim 2, wherein said composite is substantially opaque.

5. A method of forming a substantially clear dental composite comprising, (a) providing a glass filler selected from the group consisting of $SiO_2$—BaO—$Yb_2O_3$—F, $SiO_2$—$Al_2O_3$—$P_2O_5$—$Na_2O$—SrO—$Yb_2O_3$—F, $SiO_2$—$Al_2O_3$—$P_2O_5$—$Na_2O$—SrO—$Yb_2O_3$—F and $SiO_2$—BaO—$Yb_2O_3$—F—R wherein R is selected from the group consisting of $Al_2O_3$, $P_2O_5$, $Al_2O_3$—$Na_2O$, $Al_2O_3$—$K_2O$, $Al_2O_3$—$P_2O_5$, $B_2O_3$—$Na_2O$, $Al_2O_3$—$P_2O_5$—Na2O and $Al_2O_3$—$P_2O_5$—$K_2O$; and (b) providing a resin with an index of refraction approximating that of said glass filler, such that the choice of said glass filler imparts the desired translucency to said dental composite and renders said dental composite substantially radiopaque.

* * * * *